United States Patent [19]

Djuric et al.

[11] Patent Number: 4,687,864
[45] Date of Patent: Aug. 18, 1987

[54] 5-FLUORO-3-OXA-PROSTACYCLIN COMPOUNDS

[75] Inventors: Stevan W. Djuric, Evanston; Leland J. Chinn; Kurt J. Rorig, both of Glenview, all of Ill.

[73] Assignee: G. D. Searle & Co., Skokie, Ill.

[21] Appl. No.: 777,124

[22] Filed: Sep. 18, 1985

Related U.S. Application Data

[63] Continuation of Ser. No. 565,250, Dec. 23, 1983, Pat. No. 4,579,958.

[51] Int. Cl.[4] ............... C07D 309/06; C07D 307/935
[52] U.S. Cl. ..................................... 549/414; 549/9; 549/13; 549/60; 549/88; 549/214; 549/346; 549/510; 549/511; 549/465
[58] Field of Search ................ 549/465, 13, 60, 414, 549/9, 88, 346, 510, 511

[56] References Cited

U.S. PATENT DOCUMENTS 4,324,730 4/1982 Fried .................................. 549/465

Primary Examiner—Henry R. Jiles
Assistant Examiner—Bernard I. Dentz
Attorney, Agent, or Firm—John J. McDonnell; Robert H. Benson; J. Timothy Keane

[57] ABSTRACT

The present invention describes 5-fluoro-3-oxaprostacyclin ($PGI_2$) derivatives of Formula I. These compounds are useful for the treatment of platelet dysfunction, atherosclerosis, hypertension and tumor cell metastasis. Also disclosed is the process for preparing them and the appropriate intermediates.

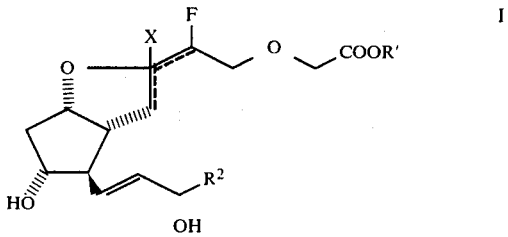

wherein $R^1$ is:
(a) Na, K, or ½ Ca, or other pharmaceutically acceptable cation
(b) $NR^3{}_2$ with the adjacent connecting oxygen omitted, where $R^3$=H, methyl, ethyl, isopropyl or a combination of these groups;
(c) Alkyl of 1 to 6 carbon atoms, either branched or straight chain
(d) Hydrogen
wherein OH on carbon 15 is optionally on carbon 16;
wherein X=$OCH_3$ or $OC_2H_5$ when neither $C_5$-$C_6$ or $C_6$-$C_7$ is a double bond and nothing if $C_5$-$C_6$ or $C_6$-$C_7$ is a double bond;
wherein $R^2$ is:
(a) A 1-8 alkyl optionally containing 1 or 2 unsaturated bond(s) and optionally substituted by methyl, dimethyl or F;
(b) A carbocyclic compound of 4-7 carbons having optionally 1 unsaturated bond and having optionally 1 carbon replaced by S or O;
(c) Phenyl;
(d) Benzyl;
(e) —$(CH_2)_m$—$R^4$ wherein m is 1-6 and $R^4$ is alkoxy or cycloalkyl;
wherein the hydroxyl on carbon 15 is in either the R or S configuration.

13 Claims, 2 Drawing Figures

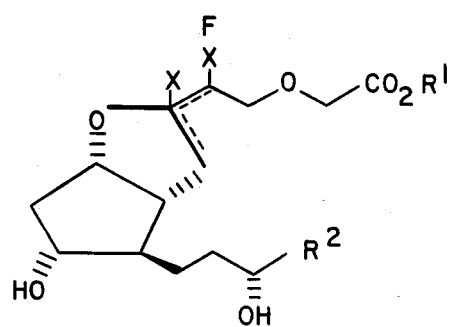
I
FIG. 1
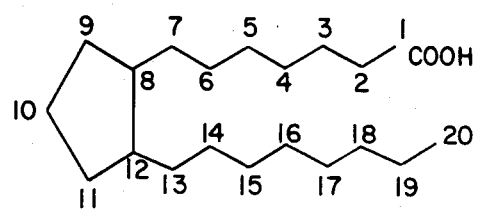
II

REACTION SCHEME

5-FLUORO-3-OXA-PROSTACYCLIN COMPOUNDS

This is a continuation of application Ser. No. 565,250, filed Dec. 23, 1983, now U.S. Pat. No. 4,579,958.

BACKGROUND OF THE INVENTION

1. Field of the Invention

This invention relates to arachidonic acid or prostaglandin derivatives and to a process for preparing them. More particularly the invention relates to novel prostacyclin derivatives, in particular $PGI_2$ derivatives. More particularly, this invention relates to $PGI_2$ derivatives of formula I, Chart A which discloses a 5-fluoro 3-oxa prostacyclin with optionally substituted $\Omega$-chain analogs.

2. Description of Prior Art

The prostaglandins and analogs are well-known organic compounds derived from prostanoic acid which has the structure and atom numbering shown in FIG. II Chart A.

As drawn hereinafter the formulas represent a particular optically active isomer having the same absolute configuration as $PGI_2$.

In the formulas, broken line attachments to the cyclopentane ring or side chain indicate substituents in alpha configuration, i.e. below the plane of the cyclopentyl ring or side chain. Heavy solid line attachments indicate substituents in beta configuration, i.e. above the plane.

For background on prostaglandins, see for example Bergstrom et al., Pharmacol Rev. 20, 1 (1968). For related compounds see Pace-Asciak et al., Biochem. 10 3657 (1971). Related compounds are described in a publication on 6-keto-prostaglandin $F_{1\alpha}$ by Pace-Asciak, J. Am. Chem. Soc. 2348 (1976) and a publication on "PGX" (6,9α-oxido-9α,15α-dihydroxyprosta(Z)5,(E)13-dienoic acid) by E. J. Corey et al., J. Am. Chem. Soc. 99, 20016 (1977).

The potential pharmaceutical value of prostacyclins and prostacyclin analogs is described by S. Moncada. Br. J. Pharmac. (1982), 76, 003–031 and by Honn et al. (U.K.) Biochemical Pharmacology (1983) 32 No. 1 1–11

The compounds of this invention may be regarded as analogs of prostacyclin and prostacyclin type compounds.

Prostacyclin, an organic compound related to prostaglandins, is (5Z)-9-deoxy-6,9α-epoxy-$\Delta^5$-$PGF_1$ and is represented by formula III of Chart A. For its synthesis and structure see for example R. A. Johnson et al., J. Am. Chem. Soc. 99, 4182 (1977) and Prostaglandins 12, 915 (1976), and E. J. Corey et al., cited above. For some of its biological properties uses see the references cited in the Johnson references. Prostacyclin is referred to as "$PGI_2$, see Anonymous Prostaglandins 13, 375 (1977).

Prostaglandins and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion, inhibition of tumor cell metastasis, and reduction of undesirable gastrointestinal effects from systemic administration of prostaglandin synthetase inhibitors.

Because of these biological responses, prostaglandins and prostacyclin-type compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi or tumor cell metastasis in mammals, including man, rabbits, and rats. For example, these compounds are useful in the treatment and prevention of myocardial infarcts, to treat and prevent postoperative surgery, and to treat conditions such as atherosclerosis, hypertension, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart lung machines. Additionally, whole blood containing these compounds can be circulated through limbs and organs, e.g. heart and kidneys, whether attached to the original body, detached and being presevved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the perfused body portion, attached or detached, to the recipient, or to two or all of those at a whole blood. These compounds are also useful in preparing platelet-rich concentrates from blood for use in treating thrombocytopenia or in chemotherapy.

Prostglandins E, F and related compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the later purpose, the compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostaglandins and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. per kg. of body weight per minute, or in a total daily dose by injection of infusion in the range about 0.01 to about 10 mg. per kg. of body weight per day, the exact dose depending on the age, weight, and condition of the patient or animal, and on the frequency and route of administration.

Prostaglandins and prostacyclin-type compounds and their analogs are also useful in mammals, including man, to treat primary neoplasms and other cancers or tumors by inhibiting the production of metastasis away from the primary lesion. These compounds can be used singularly or in combination with other anti-metastatic treatment such as chemotherapy and radiation therapy. See Honn et al., Biochemical Pharmacology, 32, 1–11, (1983) for mechanisms by which prostacyclins ($PGI_2$) are thought to prevent the metastasis by inhibiting the association of the released tumor cells with platelets and/or the blood vessel wall thereby inhibiting the formation of new metastatic foci away from the primary lesion.

To treat with an anti-metastatic amount of the prostaglandin or prostacyclin type compound, the compound is administered by infusion or injection, intravenously, subcutaneously or intramuscularly in an infusion dose range of about 0.001–50 mg/kg of body weight per minute, or in a total daily dose by injection in the range of about 0.01 to 10 mg/kg of body weight per day, the exact dose depending upon the age, weight and condition of the patient or animal, and on the frequency and route of administration.

Prostaglandins and prostacyclin-type compounds are also useful in reducing the undesirable gastrointestinal effects resulting from systemic administration of anti-inflammatory prostaglandin synthetase inhibitors, and are used for that purpose by concomitant administration of prostaglandins or prostacyclin-type compound and anti-inflammatory prostaglandin synthetase inhibitor. See Partridge et al., U.S. Pat. No. 3,781,429, for a disclosure that the ulcerogenic effect induced by certain non-steriodal and steroidal anti-inflammatory agents in rats is inhibited by concomitant oral administration of certain prostaglandins of the E and A series, including $PGE_1$, $PGE_2$, $PGE_3$, 13, 14-dihydro-$PGE_1$, and the corresponding 11-deoxy-PGE and PGA compounds. Prostaglandins and prostacyclin-type compounds are useful, for example, in reducing the undesirable gastrointestinal effects resulting from systemic administration of indomethacin, phenylbutazone, and aspirin. These are substances specifically mentioned in Partridge et al., as non-sterodial, anti-inflammatory agents. These are also known to be prostaglandin synthetase inhibitors.

The anti-inflammatory synthetase inhibitor, for example and indomethacin, aspirin, or phenylbutazone, is administered in any of the ways known in the art to alleviate an inflammatory condition, for example, in any dosage regimen and by any of the known routes of systemic administration.

The prostaglandins or prostacyclin-type compound is administered along with the anti-inflammatory prostaglandin synthetase inhibitor either by the same route of administration or by a different route. For example, if the anti-inflammatory substance is being administered orally, the prostaglandins or prostacyclin-type compound is also administered orally, or alternatively, as administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin or prostacyclin-type compound is also administered rectally. Further, the prostaglandin or prostacyclin derivative can be conveniently administered orally or, in the case of women, vaginally. It is especially convenient when the administration route is to be the same for both anti-inflammatory substance and prostaglandin or prostacyclin-type compound to combine both into a single dosage form.

The dosage regimen for the prostaglandin or prostacyclin-type compound in accord with this treatment will depend upon a variety of factors, including the type, age, weight, sex and medical condition of the mammal, the nature and dosage regimen of anti-inflammatory synthetase inhibitor being administered to the mammal, the sensitivity of the particular prostaglandin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine the administration of anti-inflammatory substance is causing undesirable gastrointestinal effects in the human or animal subject and to prescribe an effective amount of the prostaglandin or prostacyclin-type compound to reduce and then substantially to eliminate those undesirable effects.

Prostaglandin or prostacyclin-type compounds are also useful in the treatment of asthma. For example, these compounds are useful as bronchodilators or as inhibitors of mediators, such as SRS-A, and histamine which are released from cells activated by an antigen antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostaglandin or prostacyclin-type compound can be combined advantageously with other asthmatic agents, such as sympathomimetics (isoproterenol, phenylephedrine, ephedrine, etc.); xanthine derivatives (theophylline and aminophylline); and corticosteroids (ACTH and prednisolone).

Prostaglandin or prostacyclin-type compounds are effectively administered to human asthma patients by oral inhalation or aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stablize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the above ingredient suspended in an inert propellant (such as a mixture of dichloro-difluoromethane and dichloro-tetrafluoroethane) together with a co-solvent, such as ethanol, flavoring materials and stabilizers. Instead of a co-solvent there can be used a dispensing agent such as oleyl alchol. Suitable means to employ the aerosol inhalation therapy technique are described fully in U.S. Pat. No. 2,868,691 for example.

Prostaglandins or prostacyclin-type compounds are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart, the microvasculature serving the heart and to disease of the lymph vessels, for example, frostbite, isochemic cerebrovascular disease, arteriovenous fistulas, ischemic leg ulcers, phlebitis, venous insufficiency, gangrene, hepatorenal syndrome, ductus arteriosus, nonobstructive mesenteric ischemia, artritis lymphangitis and the like. These examples are included to be illustrative and should not be construed as limiting the term peripheral vascular disease. For these conditions the prostacyclin compounds are administered orally or parentally via injection or infusion directly into a vein or artery.

The dosages of such compounds are in the range of 0.01-10 $\mu$g. administered by infusions at an hourly rate or by injection on a daily basis, i.e. 1-4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No. 74/0149 referenced as Derwent Farmdoc No. 58,400 V. See Elliott et al., Lancet Jan. 18, 1975, pp. 140–142. Prostaglandins or prostacyclin-type compounds are useful in place of oxytocin to induce labor in pregnant female animals with intrauterine death of the fetus from about 20 weeks to term. For this purpose, the compound is infused intravenously at a dose of 0.01 to 50 $\mu$g. per kg. of body weight per minute until or near the termination of the second stage of labor i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostaglandins or prostacyclin type compounds are further useful for controlling the reproductive cycle in menstruating female mammals, including humans. By the term menstruating female mammals is meant animals which are mature enough to menstruate, but no so old that regular menstruation has ceased. For that purpose the prostaglandin compound is administered systemically at a dose level in the range of 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostaglandin or prostacyclin-type compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandin compounds is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, the prostacyclin compound is administered locally or systemically.

The prostaglandin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostaglandins and prostacyclin-type compounds are further useful in domestic animals as in abortifacients (especially for feedlot heifer), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin or prostacyclin-type compound is injected or applied in a feed at doses of 0.1-100 mg. per animal and may be combined with other agents such as steroids. For example, mares are given the prostaglandin compound 5 to 8 days after ovulation and return to estrus. Cattle are treated at regular intervals over a 3 week period to advantageously bring all into estrus at the same time.

Prostaglandin or prostacyclin-type compounds increase the flow of blood in the mammalian kidney, thereby increasing volume and electrolyte content of the urine. For that reason, these compounds are useful in managing cases of renal dysfunction, especially those involving blockage of a renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 100 µg. per kg. of body weight or per kg. of body weight per minute until the desire effect is obtained. Subsequent doses are given by intravenous, intramuscular, or subcutaneous injection or infusion in the range 0.05 to 2 mg. kg. of body weight per day.

Prostaglandin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosia, premalignant sun-induced keratosis, nonmalignant keratosis, acne, and seborrheic dermatitis in humans and atopic dermatitis and mange in domesticated animals. These compounds alleviate the symptoms of these proliferative skin disease; psoriasis, for example, being alleviated when a scale-free psoriasis lesion is noticeably decreased in thickness or noticeably but incompletely cleared or completely cleared.

For those purposes, such compounds are applied topically as composition including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostaglandin or prostacyclin-type compounds are useful as antilammatory agents for inhibiting chronic inflammation in mammals including the swelling and other unpleasant effects thereof using methods of treatment and dosages generally in accord with U.S. Pat. No. 3,885,041, which patent in incorporated herein by reference.

Antiplatelet substances such as $PGI_2$ are known and have been used to afford relief from the aggregate condition.

$PGI_2$, is a notably unstable substance. Although effective, $PGI_2$ often affords unwanted hypotensive effects. However, there may be occasions when such a hypotensive effect is desirable, such as in the treatment of hypertension. Also the antiplatelet aggregation effect is short lived (and the hazardous condition associated with uncontrolled platelet aggregation returns quickly). The stability of $PGI_2$ as a medicine is not satisfactory because the half period of its activity at physiological pH is only about several minutes. The instability of $PGI_2$ is considered to be due to the fact that chemically the vinyl ether structure containing a double bond at $\Delta^5$ is readily hydrated to 6-oxoprostaglandin and in vivo, it is readily metabolized by a 15-position dehydrogenase. On the other hand, $PGI_2$ is considered to be not entirely satisfactory in its pharmacological actions because its doses required for platelet aggregation inhibiting action and antihypertensive action are almost equal to each other and its selectivity of action as a medicine is inferior. Accordingly, a great deal of efforts have been made in the art to synthesize many kinds of $PGI_2$ and remedy the aforesaid defects of $PGI_2$ (see, for example, S. M. Roberts, Chemistry, Biochemistry & Pharamological Activity of Prostanoids, Pergamon Press, Oxford, 1979. New Synthetic Routes to Prostaglandins and Thromboxanes, Eds S. M. Roberts and F. Scheinmann, Academic Press, 1982).

Additional examples of stabilized $PGI_2$ structures can be found in European patent application No. 005479A2 at page 2 which is herein incorporated by reference.

PGI derivatives and prostacyclin derivatives are well known in the art as described above. U.S. Pat. Nos. 4,123,444 and 4,124,599 described PG derivatives namely prostacyclins. These patents describe 5 and 6 keto substituents as well as 9-deoxy-9-deoxo-9-hydroxymethyl substituents. The patents are described as having general prostaglandin activity. U.S. Pat. No. 4,145,535 relates to certain trans4,5-didehydro-PGI compounds which are also stated to exhibit general prostacyclin like properties. U.S. Pat. No. 4,233,121 describes certain 5 halo-6,9, oxido prostaglandin derivatives which have anticoagulant activity. European patent application No. 0054795A2/1982 discloses novel 5 or 7 monohalogenated or 5,7 dihalogenated prostacyclins useful for controlling vascular actions and inhibiting tumor matastasis.

BRIEF DESCRIPTION OF THE DRAWINGS

FIG. 1: Structure I discloses the numbering system of the 5-fluoro-3-oxa-prostacyclin compounds of this invention. Structure II discloses the numbering system of the prostane skeleton.

SUMMARY OF THE INVENTION

Figure 2:
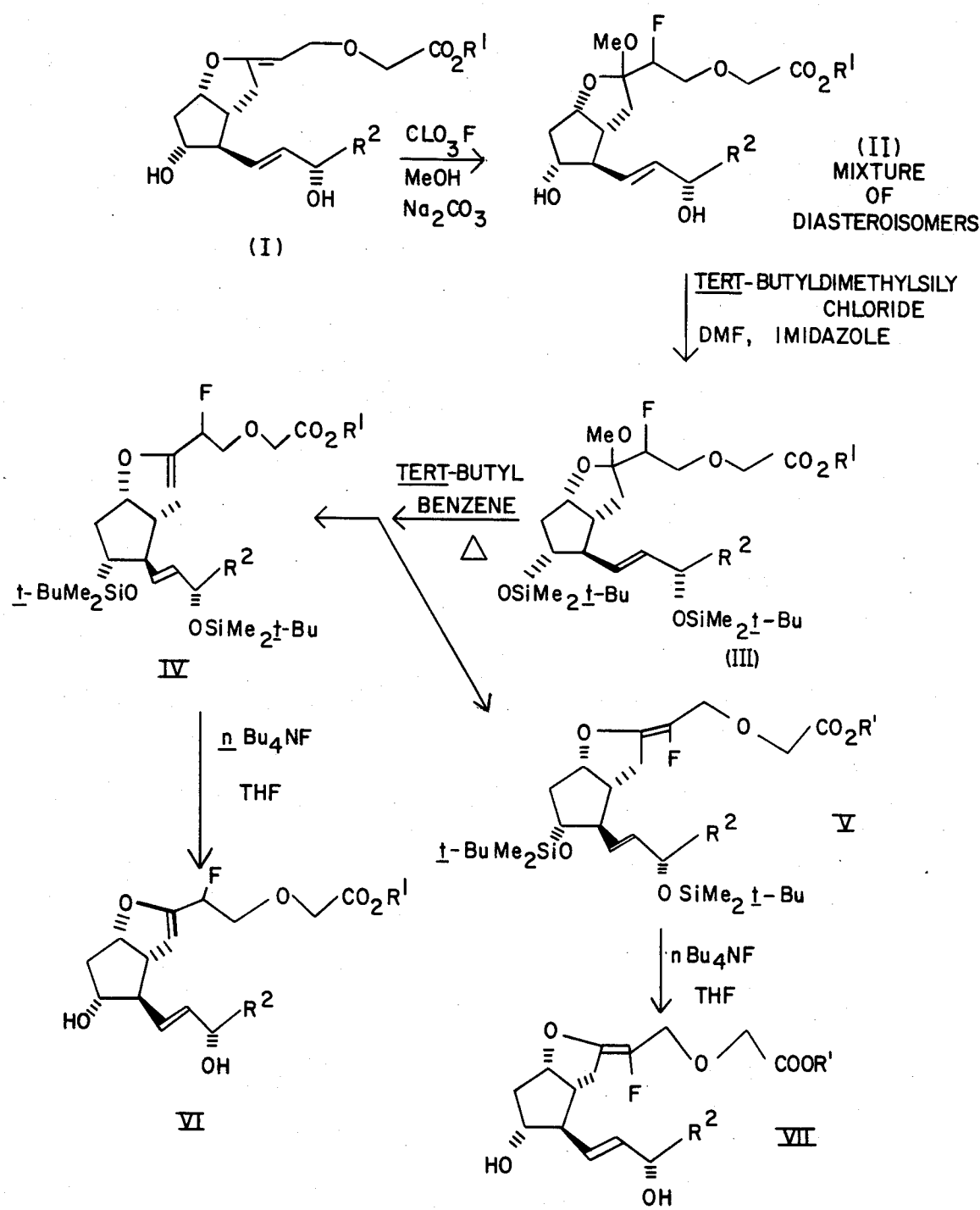
FIG. 2: Illustrates the general reaction scheme for the synthesis of the 5-fluoro-3-oxa-prostacyclins.

The present invention particularly provides:
1. A compound of formula I

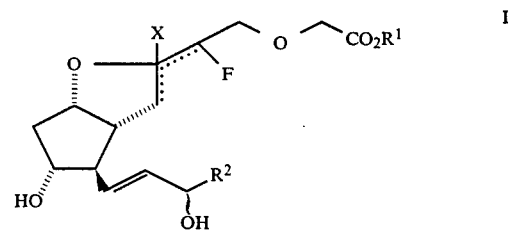

wherein $R^1$ is:
(a) Na, K, or ½Ca, or other pharmaceutically acceptable cation
(b) $NR^3_2$, where $R^3$=H, methyl, ethyl, isopropyl or a combination of these groups;
(c) Alkyl of 1 to 4 carbon atoms, either branched or straight chain
(d) Hydrogen wherein $R^2$ is:
(a) A 1–8 alkyl optionally containing 1 or 2 unsaturated bond(s) and optionally substituted by methyl, dimethyl or F;

(b) A carbocyclic compound of 4-7 carbons having optionally 1 carbon replaced by S or O;
(c) Phenyl;
(d) Benzyl;
(e) —$(CH_2)_m$—$R^4$ wherein m is 1-6 and $R^4$ is alkoxy or cycloalkyl;

wherein OH on carbon 15 is optionally on carbon 16; wherein X is $OCH_3$ or $OC_2H_5$ when neither $C_5$-$C_6$ or $C_6$-$C_7$ is a double bond and nothing if $C_5$-$C_6$ or $C_6$-$C_7$ is a double bond;

wherein the hydroxyl on carbon 15 is in either the R or S configuration.

In the compound of formula I, the $R^1$ may be methyl, ethyl, propyl, isopropyl, butyl, isobutyl and the like, pentyl, isopentyl and the like, or hexyl, isohexyl and the like. $R^3$ may be methyl, ethyl, propyl or isopropyl. $R^2$ may be methyl, ethyl, propyl, isopropyl, butyl, isobutyl and the like; pentyl, isopentyl and the like; hexyl, isohexyl and the like, heptyl, isoheptyl and the like octyl, isooctyl and the like.

$R^2$ may be ethylene, propylene, 1-butene, 2-butene, 1-pentene, 2-pentene, 3 pentene, 1-hexene, 2 hexene and the like; 1-heptene, 2-heptene and the like; 1-octene, 2-octene and the like. $R^2$ alkenes may be in either the cis or trans configuration. $R^2$ may be 2-8 alkyne optionally substituted by methyl, dimethyl or fluoro. Among the alkynes are acetylene, propyne, 1-butyne and the like, 1-pentyne and the like, 1-hexyne and the like, 1-heptyne and the like and 1 octyne and the like.

$R^2$ may be a 2-8 alkyl such a pentyl or hexyl optionally substituted by methyl, dimethyl or fluoro. $R^2$ may be a carbocyclic group of 4-7 carbons having optionally 1 unsaturated bond and optionally 1 carbon replaced by sulfur or oxygen, such as cyclohexyl, cyclopentyl, cyclobutyl, tetrahydrofuranyl, tetrahydropranyl, tetrahydrothienyl, tetrahydrothiopyranyl and the like. $R^2$ may also be phenyl or benzyl.

$R^2$ may be an alkyl containing 1-6 carbons with an alkoxy or cycloalkyl at the terminal carbon. The hydroxy at carbon 15 on $R^2$ may optionally be on carbon 16 and may be either hydroxyl in the R or S configuration. X may be methoxy or ethoxy when neither $C_5$-$C_6$ or $C_6$-$C_7$ is a double bond.

The compounds of the instant invention are novel in that, compared to natural occurring $PGI_2$, they are surprisingly more stable and are active against platelet aggregation over a longer period of time. In addition, the compounds of the present invention show a surprising and unexpected increase in "anti-platelet potency."

The instability of $PGI_2$ is largely due to the chemical readiness to decompose via the opening of an enolic cyclic ether under neutral or acidic conditions. The hydrolysed compound is either inactive or shows a marked decrease in activity. The compounds of the instant invention are more stable because of the placement of an oxygen atom at the 3 position, a fluorine bound to the 5 position and optionally an Ω-chain which retards the 15-dehydrogenase activity either sterically or electronically.

The stereochemistry of hydroxyl at carbon 15 can be in either the R or the S configuration.

By virtue of this anti-platelet aggregation activity the compounds of formula I are useful in treating platelet dysfunction in human and animals. A physician or veterinarian of ordinary skills could readily determine a subject who is exhibiting platelet dysfunction symptoms. Regardless of the route of administration selected, the compounds of the present invention are formulated into pharmaceutically acceptable dosage forms by conventional methods known to the pharmaceutical arts.

The compounds can be administered in such oral unit dosage forms such as tablets, capsules, pills, powders, or granules. They also may be administered rectally, vaginally in such forms as suppositories or creams; they may also be introduced in the form of eye drops, interparenterally, subcutaneously, or intramuscularly, using forms known to the pharmaceutical art. In general, the preferred form of administration is orally.

An effective but non-toxic quantity of the compound is employed in treatment. The dosage regimen for preventing or treating platelet dysfunction by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the agent to prevent or arrest the progress of the condition. In so proceeding, the physician or veterinarian could employ relatively low dosage at first, subsequently increasing the dose until a maximum response is obtained.

The acidic compounds of this invention can also be administered as pharmacologically acceptable basic salts such as sodium, potassium and calcium.

The starting materials used for the synthesis of the novel 3-oxa 5-fluoro prostacyclin analogs are the corresponding 3-oxaprostacyclins (Upjohn U.S. Pat. No. 3,923,861 (1975)). For example, 3-oxaPGI$_2$ tert-butylester is reacted with gaseous perchloryl fluoride in a protic solvent such as methanol. The resultant 5-fluoro-6-methoxy analog formula (II) is silylated with a trialkylsilyl chloride such as tert-butyldimethylsilyl chloride in a solvent such as anhydrous DMF containing a base such as imidazole. The resulting bis-allyl ethers (mixture of diastereo isomers or separate isomers) (III) are then converted to a mixture of the $\Delta^5$ fluoro compound (V) and the $\Delta^{6,7}$-5-fluoro compound (IV) via thermal elimination of methanol in a high boiling solvent such as refluxing tert-butyl benzene. The resulting mixture of compounds may be deprotected through exposure to a solution of an active floride source such as tetra n-butyl ammonium fluoride in a solvent such as anhydrous tetrahydrofuran. The mixture of fluoro-prostacyclins (VI) and (VII) may then be separated chromatographically.

These compounds have been shown to have platelet disaggregatory potency greater than that exhibited by the $\Delta^{6,7}$ fluoro compounds previously cited in the literature.

SYNTHESIS OF 16 HYDROXY PROSTACYCLINS

The synthesis of 16-hydroxy prostacyclins is achieved via the corresponding PGF2α analogs (as described for the natural 15-hydroxy prostacyclins).

The 16-hydroxy PGF2α analogs are synthesized via the scheme illustrated in the figure below. This synthetic procedure is described by P. W. Collins, E. Z. Dajani, R. Pappo, A. F. Gasiecki, R. G. Bianchi and E. M. Woods, J. Med. Chem. 26 786 (1983) herein incorporated by reference.

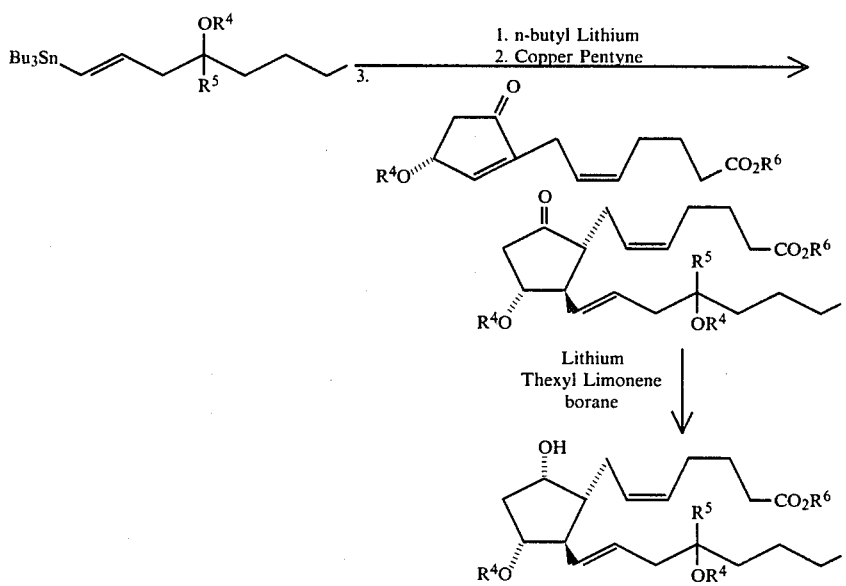

R4 can be Me3Si or Et3Si
R5 can be CH3, CH=CH
R6=Me, Et t-Bu.

In addition to the compounds described in the examples, it is also possible, for example, to manufacture according to the invention the compound given in FIG. 1, general formula I in which the hydroxyl on carbon 15 is in the R or S configuration and the OH on carbon 15 is optionally on carbon 16.

BIOLOGICAL TESTING

Inhibition of ADP-Induced platelet aggregation, in vitro.

Aggregation was determined using a Payton Dual Channel Aggregation Module. A Riker-Denshi recorder was used fo recording the aggregation curves.

Citrated whole rat blood (1 part 3.8% sodium citrate and 9 parts blood) was centrifuged to obtain platelet rich plasma.

The addition of ADP to platelet-rich plasma induces platelet aggregation. A compound was rated active if, after three separate incubations with platelet-rich plasma at $10^{-4}M$ the mean ADP-induced response is reduced by 50% or more.

DESCRIPTION OF THE PREFERRED EMBODIMENTS

Example 1

1,1-Dimethylethyl(3aβ,6aβ)[2-fluoro-2-[hexahydro-5α-hydroxy-4β-(3S*-hydroxy-1E-octenyl)-2R,2α-methoxy-2H-cyclopenta[b]furanyl]ethoxy]actetate and its methoxy epimer 1,1-Dimethylethyl(3aS,3aα,6aα)[2-[hexahydro-5β-hydroxy-4α-(3S*-hydroxy-1E-octenyl)-2H-cyclopenta-[b]furan-2Z-ylidene]ethoxy]acetate (0.15 g) was dissolved in anhydrous methanol (3 cm³) containing powdered sodium carbonate (0.3 g). The mixture was stirred vigorously at 0° C. whilst a stream of perchloryl fluoride (2-3 equivalents) was bubbled slowly through the mixture [Perchloryl fluoride had previously been condensed into a graduated burette (−78° C.)]. The mixture was allowed to warm to room temperature, stirred for 30 minutes and then partitioned between ether and water. The organic layer was separated, washed with saturated sodium chloride solution and dried (Na2SO4). Evaporaton of the volatiles in vacuo afforded 0.1 g of crude product which was chromatographed on silica gel (Merck 60, CH2Cl2/5% CH3OH). Thus obtained was 0.06 g of a mixture of the diastereoisometric fluoroprostanoids.

Spectral Data

NMR (1H, δ, CDCl3, 200 MHz) 1.45 (9H s, t-Bu) 3.17–3.28 (3H, 4s, OCH3s) 3.9 (2H, s, CH2CO2tBu) 5.3–5.55 (2H, m, olefinics) NO 4.57 (1H, m, $^{H}C{=}C°{-}$)

M.S(Isobutane CI)$^m$/eBis-TMS ether 573 (M+—CH-3OH)

IR (CHCl3) no v 1690 cm$^{-1}$

The following is the chemical structure of the compound of Example 1.

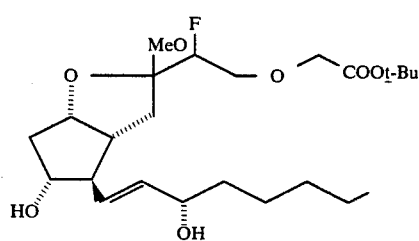

Example 2

1,1-Dimethylethyl(3aβ,6aβ)[2-fluoro-2-[hexahydro--5α-[[dimethylethyl)dimethylsilyl]oxy]-4β-(3S*-[[dimethylethyl)dimethylsilyl]oxy]-1E-octenyl)-2R,2α-methoxy-2H-cyclopenta[b]furanyl]ethoxy]actetate The mixture of methoxyfluoro PGI, derivatives (II) (0.06 g) was dissolved in anhydrous dimethyl formamide (0.5 cm³) containing tert-butyldimethylsilyl chloride (2.4 equivalents) and imidazole (5.0 equivalents). The mixture was stirred magnetically under nitrogen for 10 hours and then poured into water. The aqueous mixture was thoroughly extracted with diethyl ether and the organic layers combined, washed sequentially with water and brine and then dried (Na$_2$SO$_4$). Evaporation of the volatiles in vacuo afforded a crude residue which was purified by chromatography on silica gel (Merck 60 hexane/EtOAc, 90:10) to afford 0.07 g of pure bis silyl ethers.

The following is the chemical structure of the compound of Example 2.

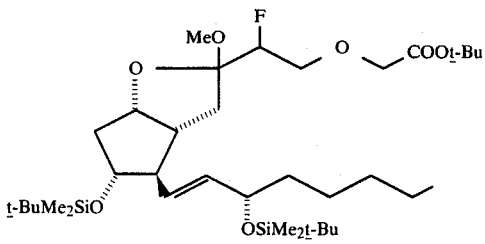

Example 3

1,1-Dimethylethyl[2-fluoro-2-[4,5,6,6aα-tetrahydro-5β-[[(dimethylethyl)dimethylsilyl]oxy]-4α[3S*-[[(dimethylethyl)dimethylsilyl]oxy]-1E-octenyl]3aS,3aαH-cyclopenta[b]furanyl]ethoxy] acetate and 1,1-dimethylethyl (3aS,3aα,6aα[2-fluoro-2-[hexahydro-5β-[(dimethylethyl)dimethylsilyl]oxy-4α-[3S*-[[(dimethylethyl)dimethylsilyl]oxy]-1E-octenyl-2H-cyclopenta[b]furan-2E-ylidene]ethoxy acetate.

The silyl ethers (III) (35 mgs) were dissolved in anhydrous tert-butyl benzene (0.5 cm$^3$) and added via syringe to tert-butyl benzene at reflux temperature. The solution was maintained at this temperature for 40 minutes and then cooled. The reaction mixture was applied directly to a florisil column (packed in hexane/0.2% triethylamine). Eluted from this column was 10 mgs of a mixture of fluoro olefins (IV) and (V) followed by 17 mgs of starting material.

Spectral Data

NMR (1H, δ, CDCl$_3$, 100 MHz) 0.1 (12H, brs, Si(CH$_3$)$_2$), 0.9 (18H, 2s, Si-t-Bu) 1.48 (9H, s, CO$_2$t-Bu)) 4.0 (2H, s, CH$_2$CO$_2$t-Bu) 4.7–5.55 (m, olefinic H's) for mixture.

The following is the chemical structure of the compounds of Example 3.

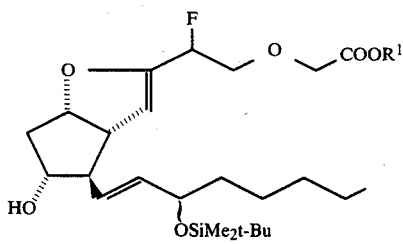

Example 4

1,1-Dimethylethyl(3aS,3aα,6aα)[2-fluoro-2-[4,5,6,6aα-tetrahyro-5β-hydroxy-4α-(3S*-hydroxy-1E-octenyl)-3aS,3aαH,-cyclopenta[b]furanyl]ethoxy]acetate and 1,1-Dimethylethyl-(3aS,3aα,6aα)[2-fluoro-2-[hexahydro-5β-hydroxy-4α(3S*-hydroxy-1E-octenyl)-2H-cyclopenta[b]furan-2E-ylidene]ethoxy]acetate A mixture of fluoro-olefins (IV) and (V) (100 mgs) were dissolved in anhydrous tetrahydrofuran (0.5 cm$^3$) containing triethylamine (1 drop) and tetra n-butylammonium fluoride (7 equivalents) and stirred overnight at RT under N$_2$. The reaction mixture was partitioned between ethyl acetate/ether and water and the organic layer separated, washed with saturated sodium chloride solution and dried (Na$_2$SO$_4$). Evaporation of the volatiles in vacuo afforded a crude residue which was purified by column chromatography to afford 1.5 mgs of exo-olefin VII and 50 mgs of endo-olefin (VI).

The following is the chemical structure of the compounds of Example 4.

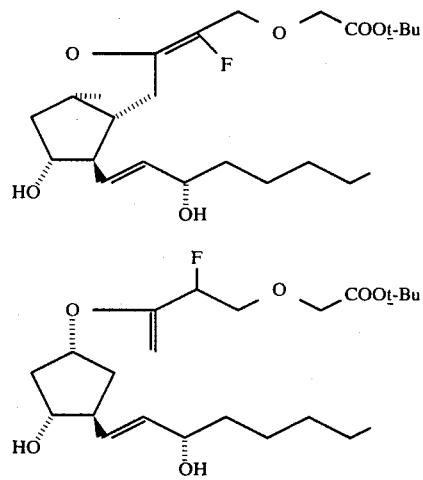

Example 5

The synthesis of lower chain (Ω) modified fluoro-prostacyclins was achieved via the corresponding 3-oxa prostacyclin. The 3-oxa prostacyclins were obtained via literature procedures, see for example, Prostaglandin synthesis, J. S. Bindra and R. Bindra, Academic Press (1977).

The starting material was the known aldehyde

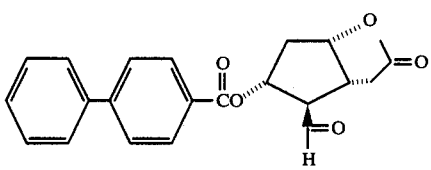

and this could be reacted in Wadsworth-Emmons fashion with a β-ketophosphonate anion such as

wherein R$^2$ is:
(a) A 1–8 alkyl optionally containing 1 or 2 unsaturated bond(s) and optionally substituted by methyl, dimethyl or F;
(b) A carbocyclic compound of 4–7 carbons having optionally 1 unsaturated bond and having optionally 1 carbon replaced by S or O;
(c) Phenyl;
(d) Benzyl;
(e) —(CH$_2$)$_m$—R$^4$ wherein m is 0–6 and R$^4$ is alkoxy or cycloalkyl;

The desired β-ketophosphonate was made via the reaction of the lithium salt of methyl (dimethyl) phosphonate with the appropriate ester

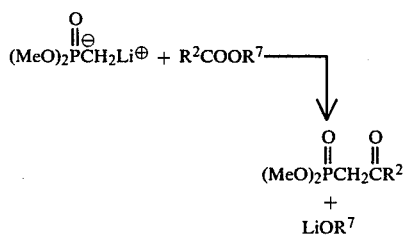

$R^7$ = Methyl, ethyl
$R^2$ = as above

Example 6

The Inhibition of ADP-Induced Platelet Aggregation

The procedure for testing platelet anti-aggregatory activity in vitro is the one described by E. R. Waskawic (Searle BRR 7710007). Aggregation was determined with a Payton Dual Channel Aggregation module. A Riken-Denshi recorder was used for recording the aggregation curves.

Citrated whole blood (1 part 3.8% sodium citrate and 9 parts blood) was centrifuged to obtain platelet rich plasma (PRP) (700 RPM for 11 mins.) in an IE centrifuge (Model PR 6000). After the PRP fraction was removed, the remainder was spun at 900×g for 15 mins. to obtain platelet poor plasma (PPP) (1800 RPM in IEC PR 6000). The number of platelets per ml PRP is determined by counting a 50 μl aliquot of PRP in a Coutter ZBI counter and channelyzer Model C-1000.

PRP is diluted with PPP 1:2 to obtain a count of approx. 25000 on the screen or $10^9$ platelets/ml PRP to evaluate the anti-aggregating agent. The module was standardized with an aliquot of PPP and that of diluted PRP.

The aggregating agent used is ADP prepared as follows:

4.7 mgs ADP (MW 427) in 10 ml saline yields a 10 μM stock solution administered in 4 μl into 400 μL PRP, of ADP disodium (MW=473).

| Vol. of stock (ml) | Volume of saline (ml) | [f] cuvette (μM) |
|---|---|---|
| 1.6 | 0.4 | 8 |
| 1.2 | 0.8 | 6 |
| 0.8 | 1.2 | 4 |
| 0.4 | 1.6 | 2 |
| 0.2 | 1.8 | 1 |

[f] = final concentration

Prostacyclin is used as the standard of antiaggregatory activity for determining the potency of compounds tested. A $10^2$M solution (to give a starting concentration of $10^{-4}$M when 4 μL is added to 400 μL PRP) is diluted serially to obtain solutions with final concentrations of $10^{-6}$, $10^{-7}$, $10^{-8}$, $10^{-9}$M.

Compounds to be screened are dissolved in absolute ethanol, saline or water to achieve a $10^{-2}$M solution if 4 μL added to PRP giving a [f] in the cuvette equal to $10^{-4}$M. Serial dilutions in saline give $10^{-5}$, $10^{-6}$ and $10^{-7}$M.

1. Determine the dose of ADP which on a standard curve would be on the linear portion and allow reversal of the aggregation curve.

2. Determine the PGI$_2$ standard curve of percentage inhibition of aggregation. Use saline in control cuvette to compare the extent of inhibition by PGI$_2$ are represented by the depth of the aggregation curve. Allow the PRP to preincubate for approximately one minute prior to the addition of prostacyclin and another minute with PGI$_2$ prior to the addition of ADP.

% Inhibition of control =

$$100.00 - \left( \frac{\text{experimental parameter}}{\text{control parameter}} \times 100 \right)$$

The % inhibition is plotted against prostacyclin dose on semilog paper. The IC$_{50}$ value is equal to the PGI$_2$ dose effecting 50% inhibition of the control response.

3. The test compound is added to PRP and preincubated for 1 minute prior to ADP administration. If the compound has an IC$_{50}$ lesser than $10^{-4}$M, it is considered to be active.

| Results | (IC$_{50}$ (Molar)) |
|---|---|
| Prostacyclin | 6 × $10^{-9}$ |
| 3-oxa prostacyclin Tert-butyl ester | 1 × $10^{-6}$ |
| 5-fluoro Δ$^{6,7}$ prostacyclin | 6 × $10^{-6}$ |
| 5-fluoro Δ$^{6,7}$ 3-oxa, prostacyclin tert-butyl ester | 4 × $10^{-6}$ |

Example 7

Ethyl (3aβ,3aβ,6aβ)[2-fluoro-2-[hexahydro-2R, 2α-methoxy-4β-[(3S*-tetrahydro-2H-pyran-2-yl)-3-[(triethylsilyl)oxy]-1E-propenyl]-5α-[(triethylsilyl)oxy]-2H-cyclopenta[b]furanyl]ethoxy acetate.

Ethyl (3aS,3aα,6aα)[2-[hexahydro-4α-[(3S*-tetrahydro-2H-pyran-2-yl)-3-[(triethylsilyl)oxy]-1E-propenyl]-5β-[(triethylsilyl)oxy]-2H-cyclopenta[b]furan-2Z-ylidene]ethoxy]acetate(1g) is dissolved in anhydrous methanol (20 cm$^3$) containing powdered sodium carbonate (2–5 equivalents). The mixture is stirred vigorously at 0° C. whilst a stream of perchloryl fluoride (2–3 equivalents) is bubbled slowly through the mixture. The mixture is allowed to warm to room temperature, stirred for 30 minutes and the partitioned between ether and water. The organic layer is separated, washed with saturated sodium chloride solution and dried (Na$_2$SO$_4$). Evaporation of the volatiles in vacuo affords a crude product which is chromatographed on silica gel (Merck 60) to afford a mixture of diastereoisomeric fluoro-prostanoids.

The following is the chemical structure of the compound of Example 7.

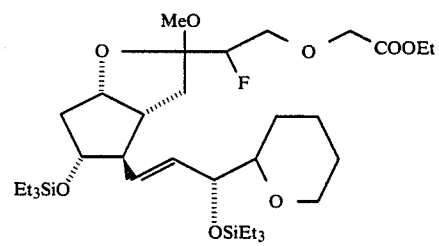

Example 8

Ethyl
(3aβ,6aβ)[2-fluoro-2-[hexahydro-5α-hydroxy-4β[3S*-hydroxy-3-(tetrahydro-2H-pyran-2-yl)-1E-propenyl]-2R,2α-methoxy-2H-cyclopenta[b]furanyl]ethoxy]acetate The mixture of fluoro-prostanoids from the previous Example 7 (0.1 g) is treated with a catalytic amount of pyridinium p-toluenesulfonate in methanol. The mixture is stirred at room temperature for 5 hours and then evaporated in vacuo. The residue is passed thru a short silica column (EtOAc as eluant) to afford the title compound as an oil (0.05 g).

The following is the chemical structure of the compound of Example 8.

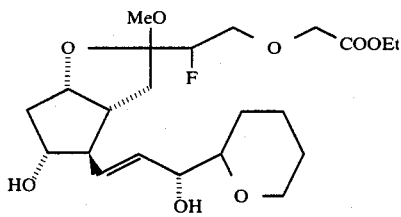

Example 8

Ethyl
(3aS,3aα,6aα)[2-fluoro-2-[hexahydro-4α-[(3S*-tetrahydro-2H-pyran-2-yl)-3-[(triethylsilyl)oxy]-1E-propenyl]-5β-[(triethylsilyl)oxy]-2H-cyclopenta[b]furan-2Z-ylidene]ethoxy]acetate and Ethyl
[2-fluoro-2-[4,5,6,6aα-tetrahydro-4α-[(3S*-tetrahydro-2H-pyran-2-yl)-3-[(triethylsilyl)oxy]-1E-propenyl]-5β-[(triethylsilyl)oxy]-3aS,3aαH-cyclopenta[b]furanyl]ethoxy acetate Ethyl (3aβ,6aβ)[2-fluoro-2-hexahydro-2R,2α-methoxy-4β-[(3S*-tetrahydro-2H-pyran-2-yl)-3-[(triethylsilyl)oxy]-1E-propenyl]-5α[(triethylsilyl)oxy]-2H-cyclopenta[b]furanyl]ethoxy acetate mixture of diastereoisomers) (0.4 g) is dissolved in anhydrous tert-butyl benzene and the mixture heated at reflux temperature for 1 hour. The cooled mixture is applied directly to a preconditioned florisil column. Repeated chromotography (hexane/ethyl acetate mixtures) affords the pure title compounds.

The following are the chemical structures of the compounds of Example 9.

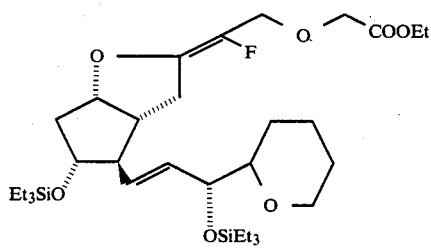

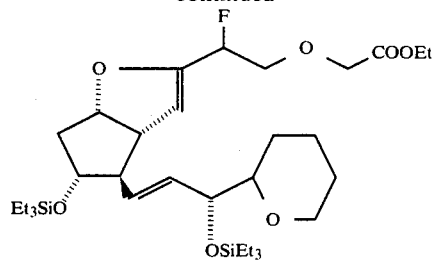

Example 10

Ethyl
(3aS,3aα,6aα)[2-fluoro-2-[hexahydro-5β-hydroxy-4α-[3S*-hydroxy-3(tetrahydro-2H-pyran-2-yl)-1E-propenyl]-2H-cyclopenta[b]furan-2Z-ylidene]ethoxy]acetate and Ethyl
[2-fluoro-2-[4,5,6,6aα-tetrahydro-5β-hydroxy-4α-[3S*-hydroxy-3-tetrahydro-2H-pyran-2-yl)-1E-propenyl]-3aS,3aαH-cyclopenta[b]furanyl]ethoxy]acetate.

Ethyl (3aS,3aα,6aα)[2-fluoro-2-[hexahydro-4α-[-(3S*-tetrahydro-2H-pyran-2-yl)-3-[(triethylsilyl)oxy]-1E-propenyl]-5β-[(triethylsilyl)oxy]-2H-cyclopenta[b]furan-2Z-ylidene]ethoxy]acetate (10 mgs) is dissolved in anhydrous THF containing tetra n-butylammonium fluoride (5 equivalents). the mixture is stirred at room temperature under nitrogen for 5 hours and then partitioned between ethyl acetate and water. The organic layer is separated, dried (Na2SO4) and evaporated in vacuo to afford the title compound as a crude oil which is purified by chromatography on florisil (hexane EToAc). The second title compound is prepared in the manner described for the first title compound. The following are the chemical structures of the compounds of Example 10.

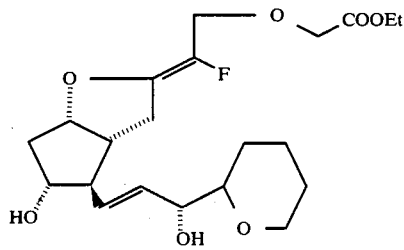

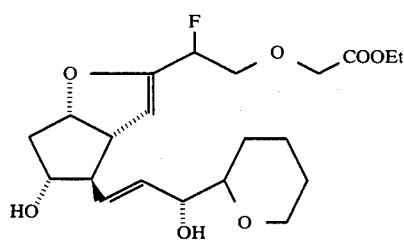

Example 11

[2-Fluoro-2-[4,5,66aα-tetrahydro-5β-hydroxy-4α-[3S*-hydroxy-3-(tetrahydro-2H-pyran-2-yl)-1E-propenyl]-3aS,3aαH-cyclopenta[b]furanyl]ethoxy]acetic acid, sodium salt.

Ethyl [2-fluoro-2-[4,5,6,6aα-tetrahydro-5β-hydroxy-4α-[3S*-hydroxy-3-tetrahydro-2H-pyran-2-yl)-1E- propenyl]-3aS,3aαH-cyclopenta[b]furanyl]ethoxy]acetate (22 mgs) is dissolved in a minimum of methanol containing 1.5 equivalents of aqueous sodium hydroxide. The mixture is stirred at 0° C. for 10 minutes and then 2 drops of water are added. The mixture is allowed to stir at room temperature for 48 hours and then evaporated under high vacuum. The residue was triturated with dry ether and redried to afford the amorphous sodium salt.

The following is the chemical structure of the compound of Example 11.

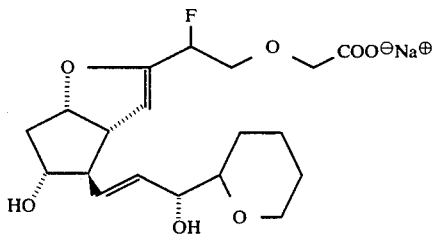

Example 12

Methyl (3aβ,6aβ)[2-(4β-(3S*-cyclopentyl-3-hydroxy-1E-propenyl)hexahydro-5α-hydroxy-2R,2α-methoxy-2H-cyclopenta[b][furanyl]-2S*-fluoroethoxy]acetate Methyl (3aS,3aα,6aα[2-[4α-(3S*-cyclopentyl-3-hydroxy-1E-propenyl]hexahydro-5β-hydroxy-2H-cyclopenta[b]furan-2Z-ylidene]-2ethoxy acetate (1 g) is dissolved in anhydrous methanol (20 cm³) containing powdered sodium carbonate (2.5 equivalents). The mixture is stirred vigorously at 0° C. whilst a stream of perchloryl fluoride (2-3 equivalents) is bubbled slowly through the mixture. The mixture is allowed to warm to room temperature, stirred for 30 minutes and then positioned between ether and water. The organic layer is separated, washed with saturated sodium chloride solution and dried (Na₂SO₄). Evaporation of the volatiles in vacuo affords the crude product which is chromatographed on silica gel to afford a mixture of diastereoisomeric fluoroprostanoids.

The following is the chemical structure of the compound of Example 12.

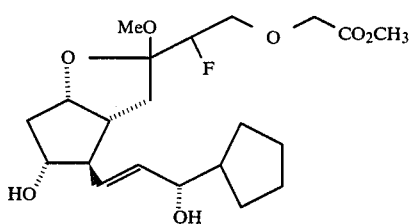

Example 13

Methyl (3aβ,6aβ)[2-(3S*-cyclopentyl-3-[[dimethylethyl)dimethylsilyl]oxy]-1E-propenyl)hexahydro-5α-[[dimethylethyl)dimethylsilyl]oxy]-2R,2α-methoxy-2H-cyclopenta[b]furanyl]-2S*-fluoroethoxy]acetate The title compound is obtained from its corresponding diol using the procedure described previously (tert-butyldimethylsilyl chloride/DMF/imidazole as a mixture of diastereoisomers.

The following is the claimed structure of the compound of Example 13.

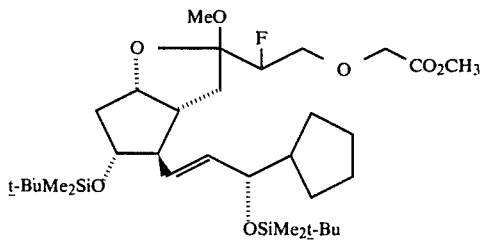

Example 14

Methyl (3aS,3aα,6aα)[2-[4α-(3S*-cyclopentyl-3-[[dimethylethyl)dimethylsilyl]oxy]-1E-propenyl)hexahydro-5β-[[dimethylethyl)dimethylsilyl]oxy]-2H-cyclopenta[b]furan-2Z-ylidene)-2-fluoroethoxy acetate and Methyl[2-[4α-(3S*-cyclopentyl-3-[[(dimethylethyl)-dimethylsilyl]oxy]-1E-propenyl)-4,5,6,6α-tetrahydro-5β-[[(dimethylethyl)dimethylsilyl]oxy]-3aS,3aαH-cyclopenta[b]furanyl]-2-fluoroethoxy]acetate The title compounds are prepared from the diastereomeric methoxy-fluoro compounds mentioned in Example 13 by heating in refluxing tert-butyl benzene (as described previously).

The following are the chemical structure of the compounds of Example 14.

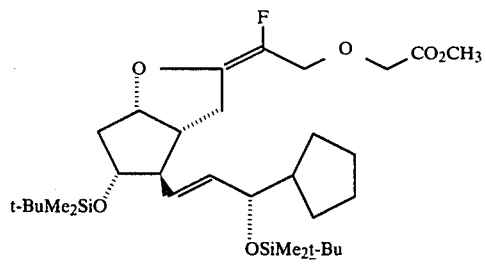

Example 15

Methyl (3aS,3aα,6aα)[2-[4α-(3S*-cyclopentyl)-3-hydroxy-1E-propenyl]hexahydro-5β-hydroxy-2H-cyclopenta[b]furan-2Z-ylidene]-2-fluoroethoxy]acetate Methyl (3aS,3aα,6aα)[2-[4α-3S*-cyclopentyl-3-[[dimethylethyl)dimethylsilyl]oxy]-1E-propenyl)hexahydro-5β-[[(dimethylethyl)dimethysilyl]oxy]-2H-cyclopenta[b]furan-2Z-ylidene)-2-fluoroethoxy]acetate is dissolved in anhydrous THF containing 5 equivalents of tetra n-butylammonium fluoride and 10 equivalents of triethylamine. The mixture is stirred at room temperature under nitrogen for 10 hours and then partitioned between ethyl acetate and water. The organic layer is separated, dried (Na₂SO₄) and evaporated in vacuo. The residue is purified by chromatography on florisil (EtOAc) to afford the title compound.

The following is the chemical structure of the compound of Example 15.

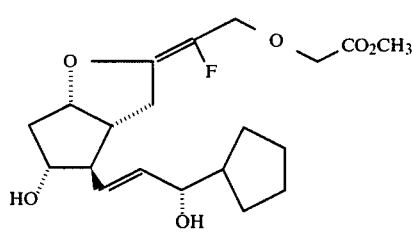

Example 16

(3aS,3aα,6aα)[2-[4α-(3S*-Cyclopentyl-3-hydroxy-1E-propenyl)]hexahydro-5β-hydroxy-2H-cyclopenta[b]furanyl-2Z-ylidene]-2-fluoroethoxy]acetic acid sodium salt Methyl (3aS,3aα,6aα)[2-[4a-(3S*-cyclopentyl-3-hydroxy-1E-propenyl]hexahydro-5β-hydroxy-2H-cyclopenta[b]furan-2Z-ylidene]-2-fluoroethoxy]acetate is dissolved in methanol (0–5 cm³) containing 1–5 equivalents of 1N NaOH at 0° C. The mixture is stirred under $N_2$ for 10 minutes and then 2 drops of water are added. The mixture is stirred at RT for 24 hours under a slow stream of nitrogen (to remove the methanol) and then evaporated under high vacuum to afford the title compound as an amorphous solid.

The following is the chemical structure of the compound of Example 16.

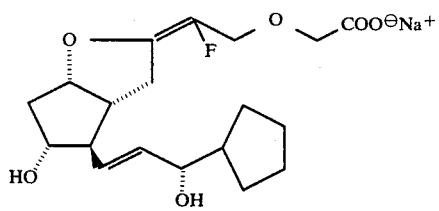

Example 17

(3aS,3aα,6aα)[2-]4α-(3S*-cyclopentyl-3-hydroxy-1E-propenyl)]hexahydro-5β-hydroxy-2H-cyclopenta[b]furan-2Z-ylidene]-2-fluoroethoxy]acetamide This compound is prepared using the procedures outlined in the text starting with (3aβ,6aβ)[2-[4β-3S*-cyclopentyl-3-hydroxy-1E-propenyl)hexahydro-5α-hydroxy-2R,2α-methoxy-2H-cyclopenta[b]furanyl]-2S*-fluoroethoxy]acetic acid (0.1 g) which is dissolved in methanol (1CM³) in a pressure bottle and chilled to −60° C. under $N_2$ and liquid ammonia (1CM³) added. The container is sealed and allowed to warm to room temperature. After 14 days the reaction bottle is opened, evacuated and product isolated as an amorphous solid.

The following is the chemical structure of the compound of Example 17.

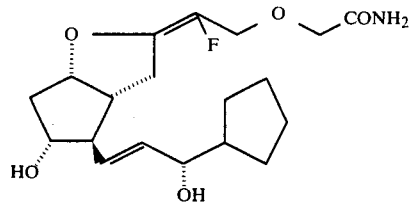

Example 18

Methyl (3aβ,6aβ)[2-fluoro-2-[hexahydro-5α-hydroxy-4β-(3S*-hydroxy-4-methyl-1E-octen-6-ynyl)-2R,2α-methoxy-2H-cyclopenta[b]furanyl]ethoxy]acetate Methyl (3aS,3aα,6aα)[2-[hexahydro-5β-hydroxy-4α-(3S*-hydroxy-4-methyl-1E-octen-6-ynyl)-2H-cyclopenta[b]furan-2Z-ylidene]ethoxy]acetate (1.5 g) is dissolved in anhydrous methanol (25 cm³) containing powdered potassium carbonate (2.5 equivalents). The mixture is stirred vigorously at 0° C. whilst a slow stream of $ClO_3F$ (2.5 equivalents) is bubbled thru the mixture. The mixture is allowed to warm to room temperature over a period of 30 minutes, it is stirred for a further 15 minutes and then it is partitioned between ether and water. The organic layer is separated, dried ($Na_2SO_4$) and evaporated in vacuo to afford the crude product. The material is purified by chromatography on silica gel (Merck 60, EtOAc) to afford the title compounds.

The following is the chemical structure of the compound of Example 18.

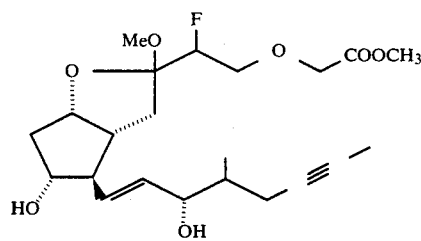

What we claim is:

1. A compound of the formula:

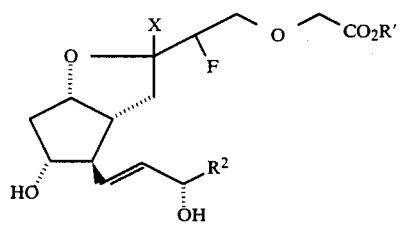

wherein $R^1$ is:
(a) a pharmaceutically acceptable cation;
(b) a branched or straight chain alkyl group of 1 to 6 carbon atoms;
(c) hydrogen;
(d) a $NR^3_2$ group with the adjacent connecting oxygen omitted, wherein each $R^3$, which may be identical or different, is hydrogen, a methyl or an ethyl group;

$R^2$ is:

(a) an aliphatic hydrocarbon group of 1 to 8 carbon atoms which is saturated or optionally contains 1 or 2 carbon-carbon unsaturated bond(s) and optionally substituted by a methyl, dimethyl or fluorine;

(b) a cycloaliphatic group of 4 to 7 ring carbon atoms which is saturated or optionally contains 1 carbon-carbon unsaturated bond and optionally has a ring carbon atom replaced by sulphur or oxygen;

(c) a phenyl group;

(d) a benzyl group;

(e) a —$(CH_2)_m$—$R^4$ group wherein m is an integer from 1 to 6 and $R^4$ is an alkoxy or cycloalkyl group; wherein the OH group on carbon 15 is optionally on carbon 16;

X is $OCH_3$ or $OC_2H_5$;

wherein the hydroxy group on carbon 15 is in either the R or S configuration.

2. The compound of claim 1 wherein X is methoxy and $R^1$ is a t-butyl or methyl group and $R^2$ is an aliphatic hydrocarbon group of 1 to 8 carbon atoms which is saturated or optionally contains 1 or 2 unsaturated bond(s) and is optionally substituted by one or two methyl groups or fluoro.

3. A compound according to claim 2 which is 1,1-Dimethylethyl(3aβ,6aβ)[2-fluoro-2-[hexahydro-5α-hydroxy-4β-(3S*-hydroxy-1E-octenyl)-2R,2α-methoxy-2H-cyclopenta-[b]furanyl]ethoxy]acetate and its methoxy epimer.

4. A compound according to claim 1 which is Methyl (3aβ,6aβ)[2-fluoro-2-[hexahydro-5α-hydroxy-4β-(3S*-hydroxy-4-methyl-1E-octen-6-ynyl)-2R,2α-methoxy-2H-cyclopenta[b]furanyl]ethoxy]acetate.

5. The compound of claim 1 wherein $R^1$ is methyl, ethyl, a Na cation or $NH_2$; and $R^2$ is a cycloaliphatic group of 4 to 7 ring carbon atoms which is saturated or optionally contains 1 carbon-carbon unsaturated bond and optionally has a ring carbon atom replaced by sulfur or oxygen.

6. A compound according to claim 5 which is Ethyl (3aβ,6aβ)[2-fluoro-2-[hexahydro-5α-hydroxy-4β[3S*-hydroxy-3-(tetrahydro-2H-pyran-2yl)-IE-propenyl]-2R,2α-methoxy-2H-cyclopenta[b]furanyl]ethoxy]acetate.

7. A compound according to claim 5 which is Methyl (3aβ,6aβ)[2-[4β-(3S*-cyclopentyl-3-hydroxy-1E-propenyl)hexahydro-5α-hydroxy-2R,2α-methoxy-2H-cyclopenta[b][furanyl]-2S*-fluoroethoxy]acetate.

8. A compound of the formula:

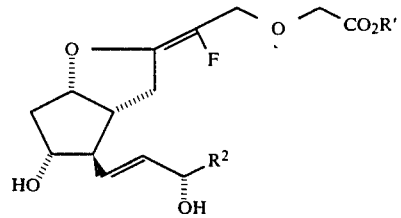

wherein $R^1$ is:

(a) a pharmaceutically acceptable cation;

(b) a branched or straight chain alkyl group of 1 to 6 carbon atoms;

(c) hydrogen;

(d) a $NR^3{}_2$ group with the adjacent connecting oxygen omitted, wherein each $R^3$, which may be identical or different, is hydrogen, a methyl or an ethyl group;

$R^2$ is:

(a) a cycloaliphatic group of 4 to 7 ring carbon atoms which is saturated or optionally contains one carbon-carbon unsaturated bond and optionally has a ring carbon atom replaced by sulphur or oxygen;

(b) a —$(CH_2)_m$—$R^4$ group wherein m is an integer from 1 to 6 and $R^4$ is an alkoxy or cycloalkyl group; wherein the OH group on carbon 15 is optionally on carbon 16;

wherein the hydroxy group on carbon 15 is in either the R or S configuration.

9. The compound according to claim 8 wherein $R^1$ is a methyl group, an ethyl group, a Na cation or $NH_2$ and $R^2$ is a cycloaliphatic group of 4 to 7 ring carbon atoms which is saturated or optionally has 1 unsaturated bond and/or optionally 1 carbon replaced by sulphur or oxygen.

10. A compound according to claim 9 which is Methyl (3aS,3aβ,6aα)[2-[4α-(3S*-cyclopentyl)-3-hydroxy-1E-propenyl]hexahydro-5β-hydroxy-2H-cyclopenta[b]furan-2Z-ylidene]-2-fluoroethoxy]acetate.

11. A compound according to claim 9 which is (3aS,3aα,6aα)[2-[4α-(3S*-Cyclopentyl-3-hydroxy-1E-propenyl)]hexahydro-5β-hydroxy-2H-cyclopenta[b]furanyl-2Z-ylidene]-2-fluoroethoxy]acetic acid sodium salt.

12. A compound according to claim 9 which is (3aS,3aα,6aα)[2-[4α-(3S*-cyclopentyl-3-hydroxy-1E-propenyl)]hexahydro-5β-hydroxy-2H-cyclopenta[b]furan-2Z-ylidene]-2-fluoroethoxy]acetamide.

13. A compound according to claim 8 which is Ethyl (3aS,3aα,6aα)[2-fluoro-2-[hexahydro-5β-hydroxy-4α-[3S*-hydroxy-3(tetrahydro-2H-pyran-2-yl)-1E-propenyl]-2H-cyclopenta[b]furan-2Z-ylidene]ethoxy]acetate.

* * * * *